United States Patent
Bose et al.

(10) Patent No.: US 9,615,832 B2
(45) Date of Patent: Apr. 11, 2017

(54) ANEURYSM OCCLUSION SYSTEM AND METHOD

(71) Applicant: Penumbra, Inc., Alameda, CA (US)

(72) Inventors: Arani Bose, New York, NY (US); Vikas Gupta, San Leandro, CA (US); Dave Barry, Livermore, CA (US); Delilah Hui, American Canyon, CA (US); Stephen Pons, San Francisco, CA (US); Aleksandr Leynov, Walnut Creek, CA (US)

(73) Assignee: Penumbra, Inc., Alameda, CA (US)

( * ) Notice: Subject to any disclaimer, the term of this patent is extended or adjusted under 35 U.S.C. 154(b) by 973 days.

(21) Appl. No.: 13/906,714

(22) Filed: May 31, 2013

(65) Prior Publication Data

US 2013/0261730 A1 Oct. 3, 2013

Related U.S. Application Data

(63) Continuation-in-part of application No. 13/312,816, filed on Dec. 6, 2011, now abandoned, and a
(Continued)

(51) Int. Cl.
*A61F 2/06* (2013.01)
*A61B 17/12* (2006.01)
(Continued)

(52) U.S. Cl.
CPC ........ *A61B 17/12118* (2013.01); *A61F 2/885* (2013.01); *A61F 2/91* (2013.01);
(Continued)

(58) Field of Classification Search
CPC ...... A61F 2/01; A61F 2/07; A61F 2/82; A61F 2/885; A61F 2/86; A61F 2/88; A61F 2/915;
(Continued)

(56) References Cited

U.S. PATENT DOCUMENTS 6,663,607 B2    12/2003   Slaikeu et al.
7,105,018 B1 *   9/2006   Yip .......................... A61F 2/90
                                                                                                       623/1.15
(Continued)

FOREIGN PATENT DOCUMENTS

WO    WO 02/09617 A1    2/2002
WO    WO 2007/117645 A2    10/2007

OTHER PUBLICATIONS

European search report and opinion dated Dec. 2, 2015 for EP Application No. 1379923.1.
(Continued)

*Primary Examiner* — Jonathan Miles
*Assistant Examiner* — Kankindi Rwego
(74) *Attorney, Agent, or Firm* — Wilson Sonsini Goodrich & Rosati

(57) ABSTRACT

An aneurysm occlusion system includes a device positionable within a cerebral blood vessel covering a neck of an aneurysm on the blood vessel. The device includes an expandable tubular element having a lumen surrounded by a sidewall including a plurality of gaps. When expanded, the tubular element includes longitudinal standards arrayed helically in a proximal to distal direction. The standards support struts and the gaps are defined between adjacent struts and are sufficiently large to permit delivery of embolic coils or other embolic materials therethrough.

9 Claims, 20 Drawing Sheets

Related U.S. Application Data continuation-in-part of application No. 11/784,236, filed on Apr. 6, 2007, now abandoned.

(60) Provisional application No. 61/655,116, filed on Jun. 4, 2012, provisional application No. 60/790,160, filed on Apr. 7, 2006.

(51) Int. Cl.

| | | |
|---|---|---|
| *A61F 2/88* | (2006.01) | |
| *A61F 2/966* | (2013.01) | |
| *A61F 2/91* | (2013.01) | |
| *A61F 2/915* | (2013.01) | |
| *A61F 2/82* | (2013.01) | |
| *A61F 2/95* | (2013.01) | |
| *A61M 25/06* | (2006.01) | |

(52) U.S. Cl.
CPC .............. *A61F 2/966* (2013.01); *A61F 2/915* (2013.01); *A61F 2002/823* (2013.01); *A61F 2002/825* (2013.01); *A61F 2002/9505* (2013.01); *A61F 2002/9665* (2013.01); *A61F 2230/0006* (2013.01); *A61F 2230/008* (2013.01); *A61F 2230/0069* (2013.01); *A61F 2230/0091* (2013.01); *A61M 2025/0681* (2013.01)

(58) Field of Classification Search
CPC .................. A61F 2/95; A61F 2002/823; A61F 2002/825; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583; A61F 2002/91591; A61B 17/12118

See application file for complete search history.

(56) References Cited

U.S. PATENT DOCUMENTS

| | | |
|---|---|---|
| 8,333,796 B2 | 12/2012 | Tompkins et al. |
| 2003/0040772 A1* | 2/2003 | Hyodoh ................ A61F 2/90 606/200 |
| 2004/0193246 A1 | 9/2004 | Ferrera |
| 2005/0165470 A1* | 7/2005 | Weber .................. A61F 2/88 623/1.15 |
| 2005/0177221 A1* | 8/2005 | Mustapha ............. A61F 2/856 623/1.11 |
| 2007/0239261 A1 | 10/2007 | Bose et al. |
| 2009/0036976 A1 | 2/2009 | Beach et al. |
| 2011/0184454 A1 | 7/2011 | Barry et al. |

OTHER PUBLICATIONS

International search report and written opinion dated Sep. 13, 2013 for PCT/US2013/043931.

* cited by examiner

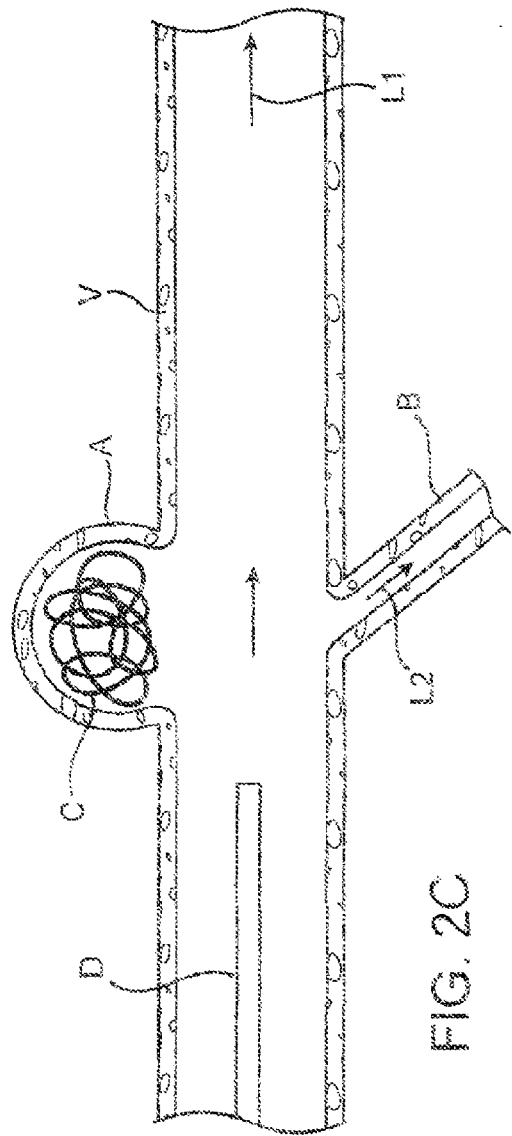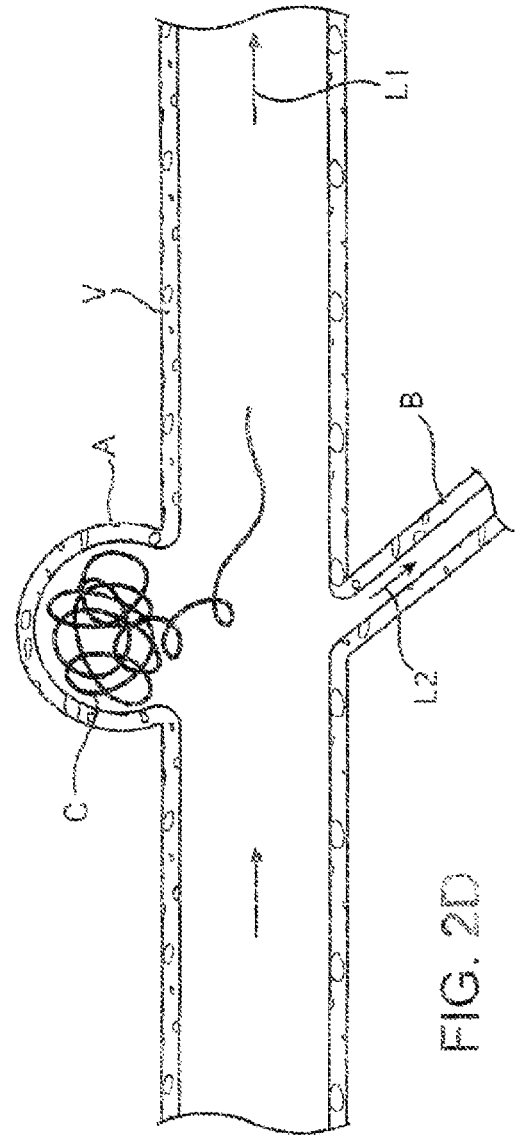

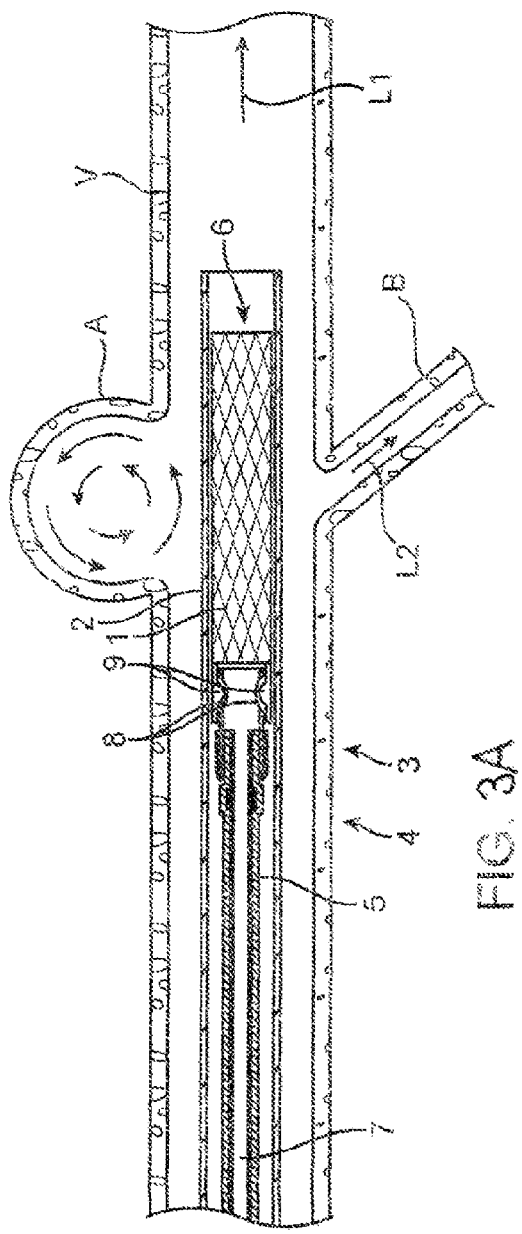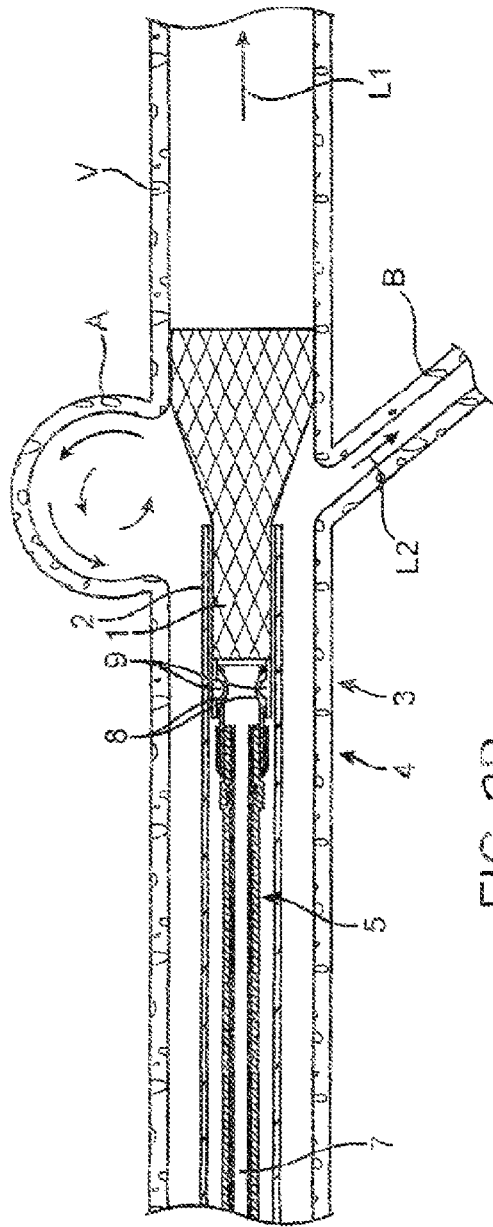
FIG. 3A
FIG. 3B

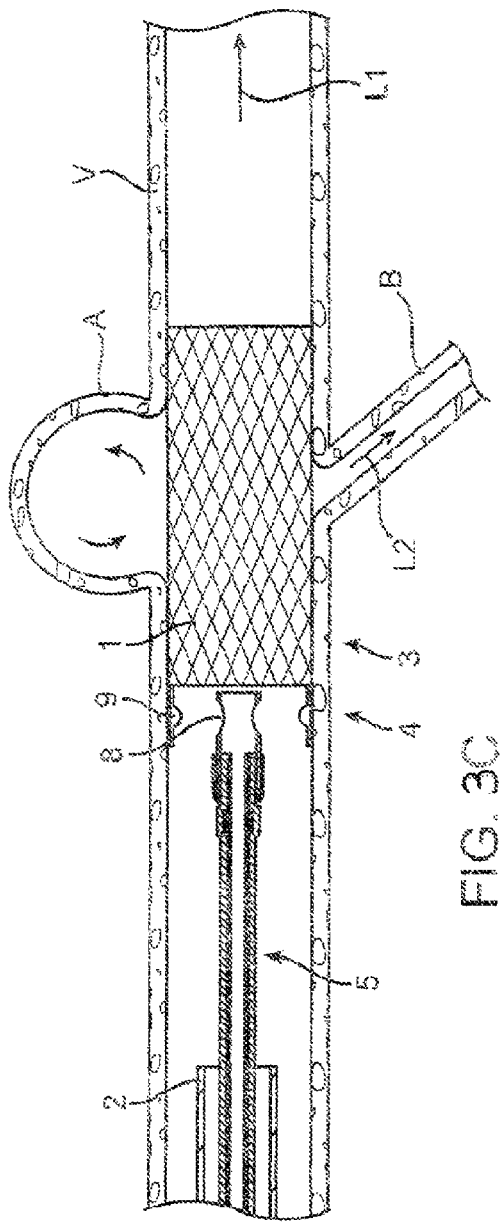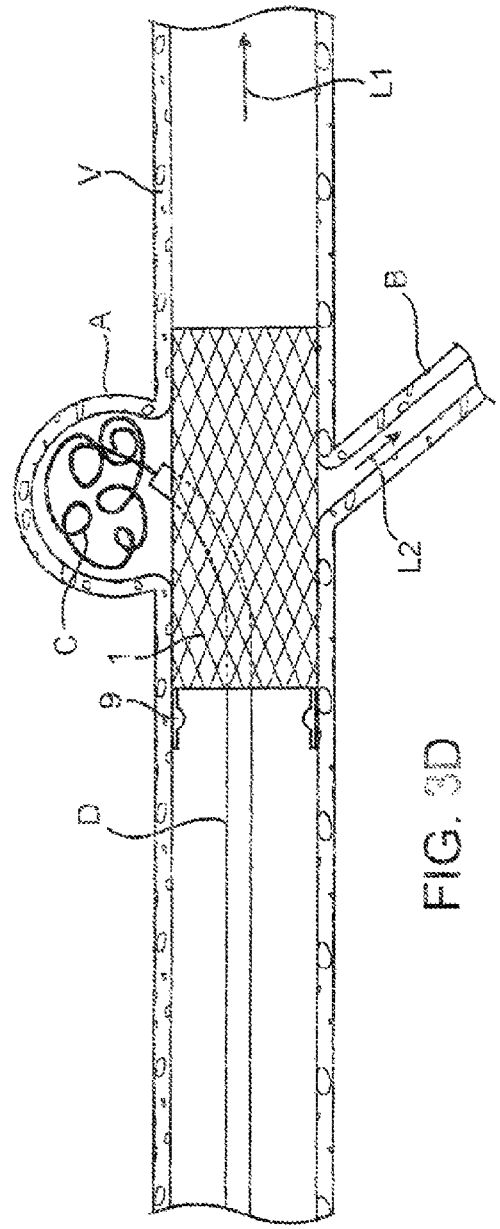

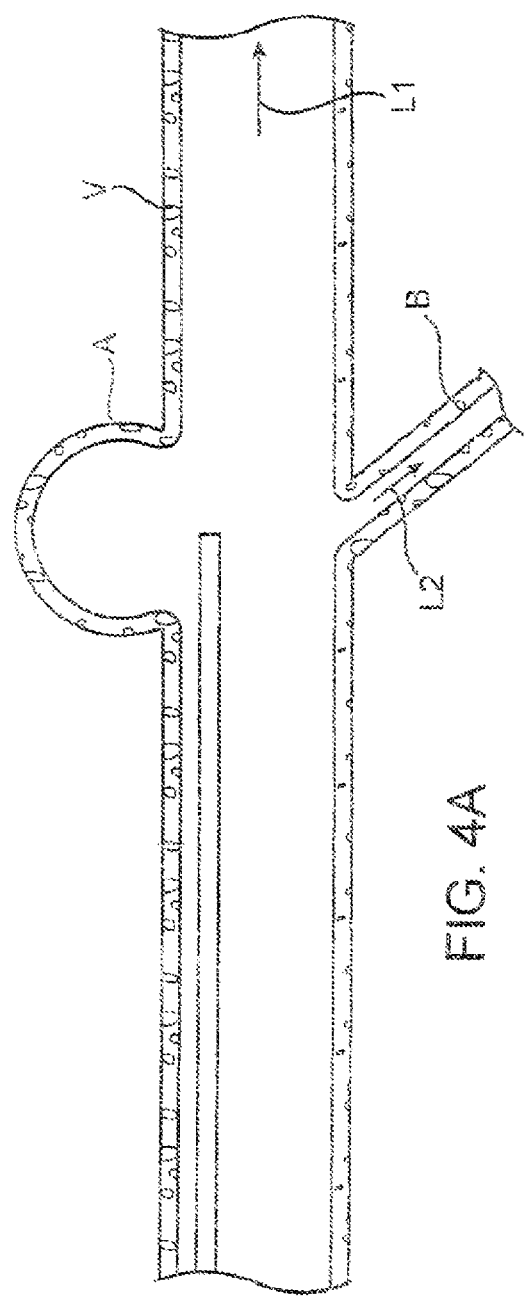
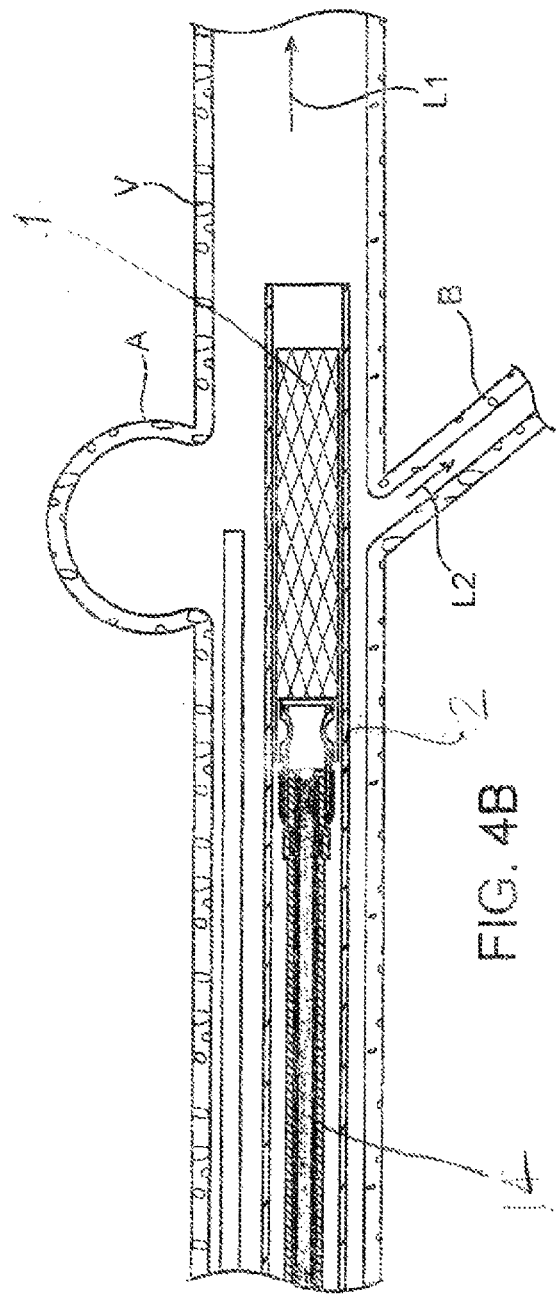
FIG. 4A
FIG. 4B

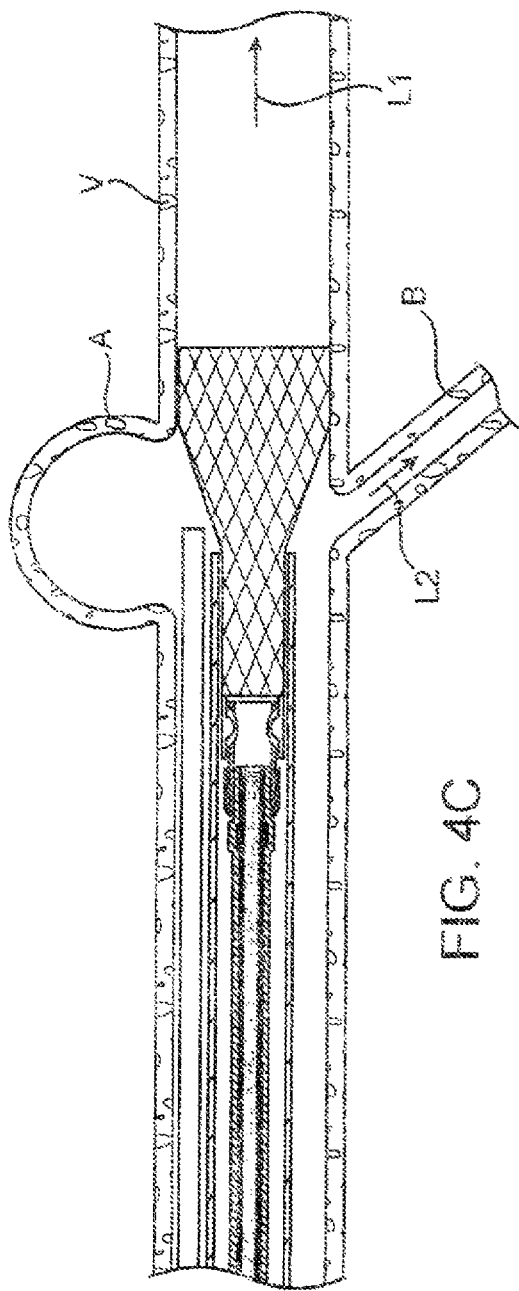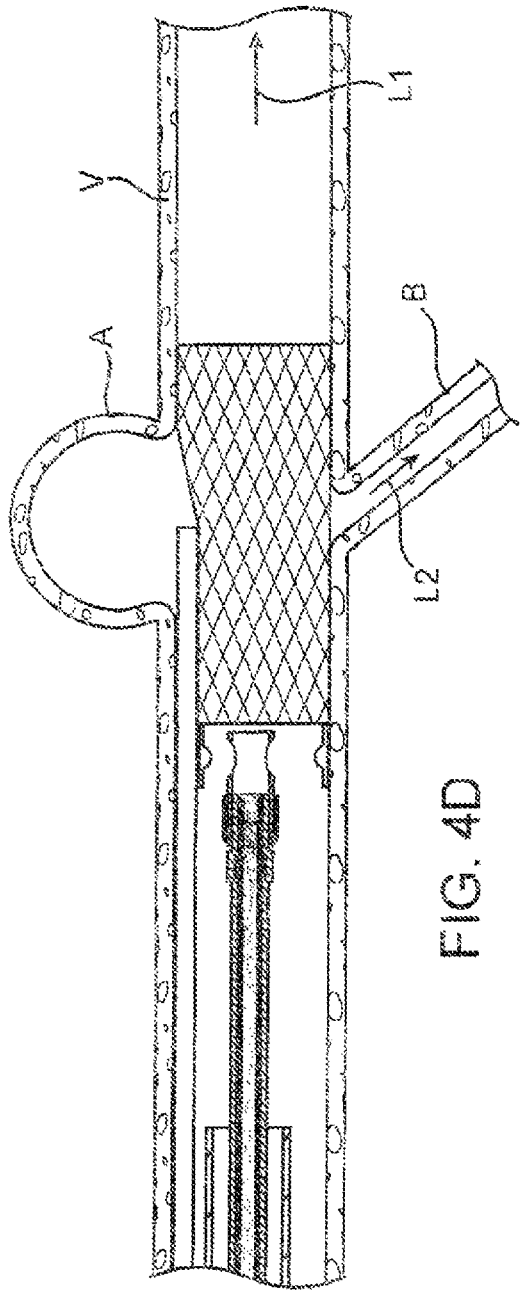

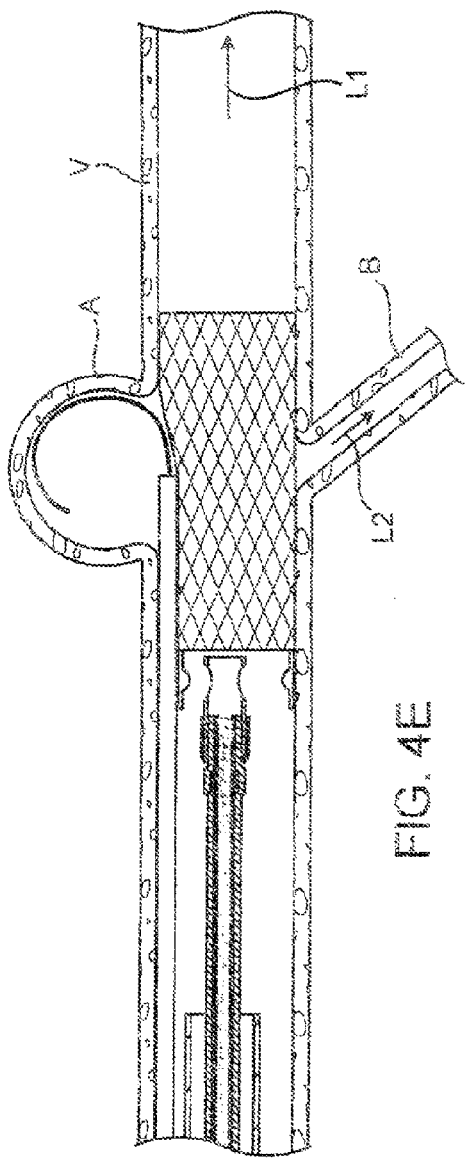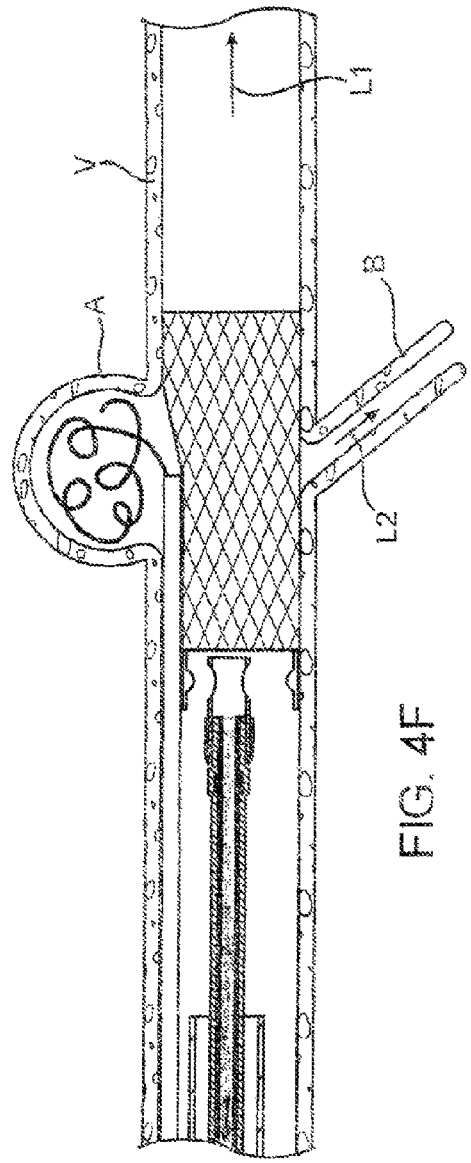
FIG. 4E
FIG. 4F

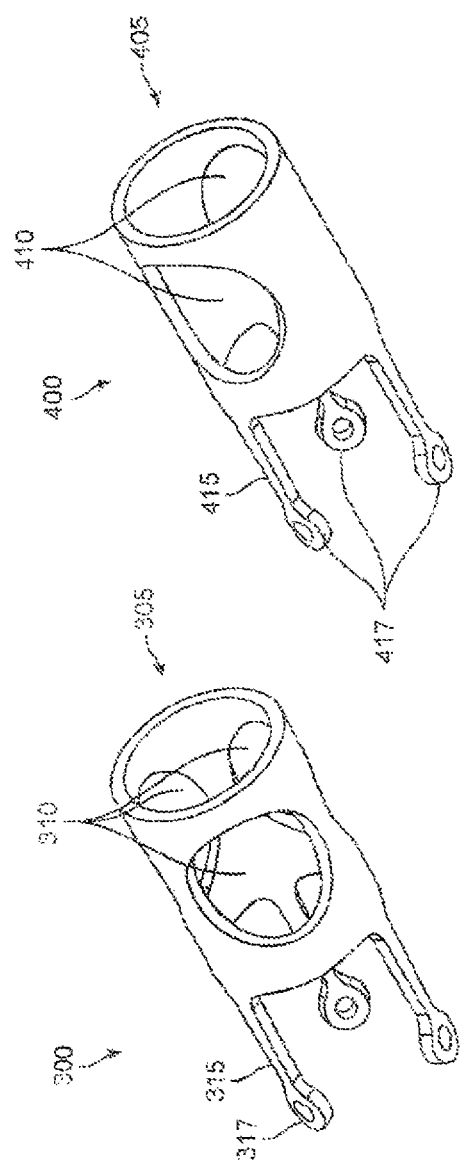

ANEURYSM OCCLUSION SYSTEM AND METHOD

CROSS-REFERENCE TO RELATED APPLICATIONS

This application claims priority to U.S. Provisional Application No. 61/655,116, filed Jun. 4, 2012; and is a continuation-in-part of U.S. patent application Ser. No. 13/312,816, filed Dec. 6, 2011; and is also a continuation-in-part of U.S. patent application Ser. No. 11/784,236, filed Apr. 6, 2007, which claims priority to U.S. Provisional Application Ser. No. 60/790,160, filed Apr. 7, 2006, the disclosures of which are incorporated herein by reference.

BACKGROUND OF THE INVENTION

Field of the Invention

The present invention relates generally to the fields of systems and methods for treatment of aneurysm, including implanting one or more intravascular devices for occlusion of the aneurysm.

An aneurysm is an abnormal ballooning of a region of a blood vessel wall due to weakening of the wall tissue. While aneurysms can occur in any artery of the body, a large percentage of aneurysm are found in the cerebral blood vessels. If left untreated, such aneurysms can rupture, leading to life threatening hemorrhaging in the brain which can result in death or severe deficit.

Aneurysms that do not rupture can form blood clots which can break away from the aneurysm potentially causing a stroke. In some patients, aneurysm can put pressure on nerves or brain tissue, causing pain, abnormal sensations, and/or seizures.

One current practice for treatment of an aneurysm includes surgical placement of an aneurysm clip across the aneurysm to prevent blood flow into the aneurysm. Naturally, this procedure requires highly invasive brain surgery and thus carries many risks.

In a less invasive catheter-based technique for aneurysm treatment, filler material is carried through the vasculature to the site of the aneurysm and used to pack the aneurysm. Materials used for this purpose include platinum coils and cellulose acetate polymer to fill the aneurysm sac. While these techniques have had some success, questions remain concerning their long-term effectiveness, ease of use, as well as their potential for rupturing the aneurysm or triggering clot formation. In addition, there is some risk of post procedure migration of embolic material from the aneurysm into the parent blood vessel.

According to another prior art aneurysm treatment, a mesh or braided stent-like device is positioned within a blood vessel such that it bridges the aneurysm, blocking flow of blood into the aneurysm. A problem encountered with devices of this type is that the sidewalls of the devices not only occlude blood flow into the aneurysm, but they will also block flow between the blood vessel and any side branch vessels that the stent happens to cover. See FIG. 1A, which shows a blood vessel V, aneurysm A, and side branch vessel B. In some prior art modifications to the stent-type devices, the devices include sidewalls that are not occlusive around the full circumference of the device. In implanting these devices, the physician must make certain that the occlusive portion of the device's circumference covers the aneurysm and not any of the side branch vessels.

Returning to the aneurysm coil embolization solution mentioned above, a typical procedure is illustrated in FIGS. 2A-2D. A typical occlusion coil is a wire coil having an elongate primary shape with windings coiled around a longitudinal axis. It is constrained in an elongate configuration or primary shape within the catheter for delivery through the interior of the catheter. The catheter is introduced into the femoral artery and navigated through the vascular system under fluoroscopic visualization. The catheter distal end is positioned at the site of an aneurysm within the vasculature of the brain. (See FIG. 2A, illustrating catheter distal end D as it is being positioned at the site of aneurysm A.)

With proper positioning of catheter distal end D confirmed, the coil is passed from the catheter into the aneurysm. The coil reverts to a three dimensional configuration after release from the distal end of the catheter into the interior of the aneurysm. Once released from the catheter, the coil assumes a secondary shape selected to optimize filling of the aneurysm cavity, and the catheter may be withdrawn from the vessel. (See FIGS. 2B-2C, illustrating the release of coil C into aneurysm A.) Multiple coils may be introduced into a single aneurysm cavity for optimal filling of the cavity. The deployed coils serve to block blood flow into the aneurysm and reinforce the aneurysm against rupture. The implants are intended to embolize the blood inside the aneurysm in order to diminish additional blood flow into the aneurysm. Eventually the embolization completely closes the aneurysm to further flow of blood into the aneurysm. For a more detailed description of embolic coils and related methods, see commonly owned U.S. patent application Ser. No. 12/498,752 and No. 12/695,035.

In some cases, there is a significant risk of migration of the coils or other implants out of the aneurysm and into the parent vessel after delivery and deployment (or release or detachment) of the coils. This is especially a risk in the case of a "wide neck" aneurysm. (See FIG. 2D). Migration of a coil or coils into the circulatory system is undesirable and can lead to occlusion of the parent vessel, other vessels, as well as lead to other unintended effects.

In such cases, it may be desirable to "bridge" the neck of the aneurysm with a device prior to the delivery of embolic implants. Such a bridge device may be a generally tubular structure that is positionable via catheter within the parent vessel, covering the neck of the aneurysm. Positioning of such a device is typically performed with the assistance of a guidewire and fluoroscopic visualization. The generally tubular aneurysm bridge is deployed across the neck of the aneurysm and allowed to expand into contact with the vessel walls. Embolic coils are then delivered into the aneurysm through voids in the "walls" of the tubular bridge.

Shortcomings of prior art attempts to bridge the neck of an aneurysm prior to embolic coil delivery include difficulties with tracking and deployment of the device, problems resheathing and repositioning the device, entanglement between the coil delivery catheter and the bridge device, and problems with portions of the device "bulging" into the aneurysm. Therefore, there remains a need for smooth, kink-free tracking, deployment, repositioning, and reliable, uniform deployment. There also remains a need for a sufficiently flexible device having adequate column strength.

BRIEF DESCRIPTION OF THE DRAWINGS

FIG. 2A-2D illustrate some of the steps of a method of implanting one or more embolic coils into an aneurysm in a blood vessel.

FIGS. 3A-3E illustrate some of the steps of a method of implanting a device to bridge the neck of an aneurysm and then implanting one or more embolic coils into the aneurysm.

FIG. 4A-4G illustrate some of the steps of an alternative method of implanting a device to bridge the neck of an aneurysm and then implanting one or more embolic coils into the aneurysm.

FIGS. 7A-7C are cross-sectional end views of the embodiment of FIG. 7 taken along section lines A, B, and C.

FIG. 8 illustrates the cut tube as though it were longitudinally cut and flattened into a sheet before twisting, so that the pattern features may be more easily viewed.

FIG. 9 illustrates the device as though it were longitudinally cut and flattened into a sheet before it is twisted, so that its features may be more easily viewed.

FIG. 11 illustrates the device as though, after shape setting to include a right hand twist, it were longitudinally cut and unrolled so that its features are more easily viewed.

FIG. 13 is a perspective view of a pusher tip according to the invention.

FIG. 14 is a perspective view of an alternative embodiment of the pusher tip of FIG. 11.

DETAILED DESCRIPTION OF THE DRAWINGS

Figure 1:
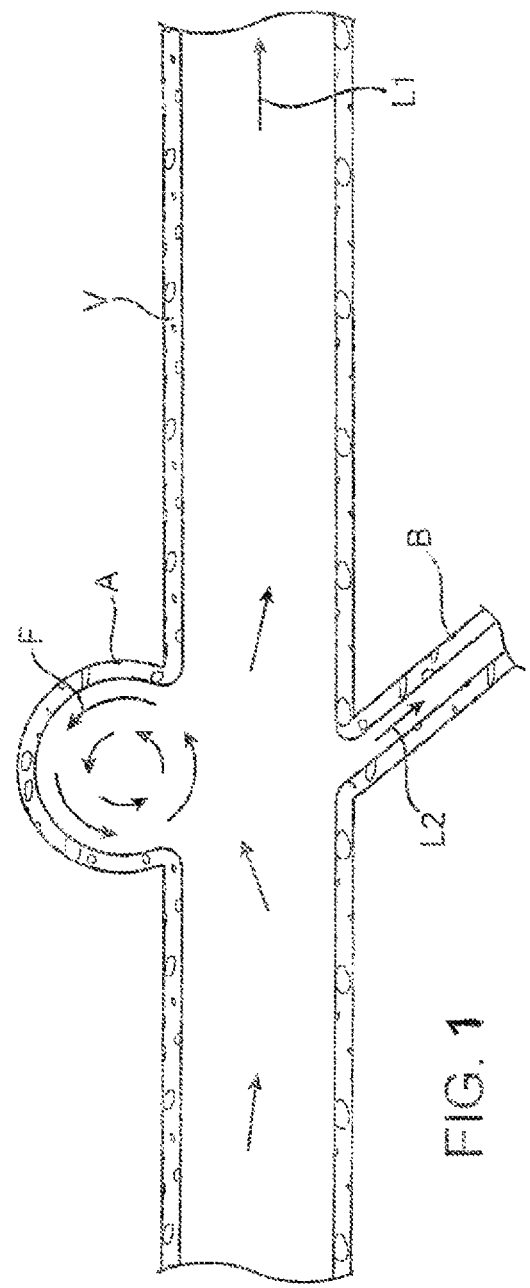
FIG. 1 schematically illustrates an aneurysm in a blood vessel and the corresponding blood flow.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be routine undertaking for those of ordinary skill in the art having the benefit of this disclosure. The aneurysm occlusion system disclosed herein boasts a variety of inventive features and components that warrant patent protection, both individually and in combination.

In FIG. 3A, a system for bridging the neck of an aneurysm before delivering embolics to the aneurysm is illustrated during a step of a method according to the invention. (An alternative exemplary method is discussed below in relation to a description of FIGS. 4A-4G.) FIG. 3A illustrates a system after the step of positioning the system in a vessel V having aneurysm A. The aneurysm bridge device and accompanying delivery system include aneurysm bridge device 1, sheath 2 and pusher 5. A guide wire (not pictured) may also be utilized in the step of positioning the system in a vessel. Aneurysm bridge device is a generally tubular device capable of being retained in a reduced profile delivery configuration. The aneurysm bridge device 1 is proportioned to be implanted within the cerebral vasculature including, but not limited to, the Internal Carotid Artery, External Carotid Artery, Vertebral Artery, Basilar Artery, Middle Cerebral Artery, Anterior Cerebral Artery, and the Posterior Cerebral Artery.

Generally speaking, aneurysm bridge device 1 is a tubular device having central lumen 6. It is retained in a reduced profile delivery configuration by sheath 2, and it is capable of expanding into contact with the vessel walls when released or deployed to a larger diameter configuration. Preferred devices 1 are expandable to an outer diameter in the range of 2.0 mm-6.0 mm. The user may be provided with a set of multiple aneurysm bridge devices of different diameters and different lengths so that the device with the most appropriate dimensions may be chosen for the procedure.

Suitable materials for device 1 include shape memory materials including superelastic Nitinol or shape memory polymers, or other materials such as stainless steel, composite materials, or combinations of metals and polymeric materials. In a preferred embodiment, the aneurysm bridge device 1 may be formed by laser cutting features into a length of superelastic Nitinol tubing, then chemically processing and shape-setting the material one or more time using methods known to those skilled in the art. The device may then be chilled to below its shape memory transition temperature and loaded onto pusher 5 and retained by sheath 2.

In the example of a method according to the invention illustrated beginning in FIG. 3A, proximal end 3 of aneurysm bridge device 1 is disposed upon the distal end 4 of pusher 5 while being retained by sheath 2. Sheath 2 is an elongate tubular catheter preferably formed of a polymeric material such as Pebax nylon, urethane, PTFE, Polyimide, metals such as Stainless Steel, Platinum, etc., or other suitable material. A central lumen extends the length of sheath 2. The sheath is proportioned for passage through cerebral vasculature, and may have an outer diameter in the range of 1 mm-3 mm.

Pusher 5 is an elongate tubular member having optional lumen 7. The pusher may be formed of suitable polymers, metals, and/or composite materials. Distal end or tip 4 of pusher 5, which is described in greater detail below in a description of FIGS. 11-14, includes apertures 8. When loaded onto distal tip 4, device 1 is threaded over pusher 5, and positioned so that bumps 9 of its proximal end 3 are aligned with, or inserted into, apertures 8. Bumps 9 may alternatively be projections, tabs, posts, clips, or any structures, preferably male, that are suitable for engaging apertures 8. Similarly, apertures 8 may alternatively be pockets, holes, hollows, grooves, or any structures, preferably female, for receiving bumps 9. Sheath 2 retains bumps 9 in engagement with apertures 8 as it retains aneurysm bridge device 1 in a reduced profile configuration. Device 1 remains in the reduced profile configuration during tracking of the device under fluoroscopic visualization to a treatment site within the vasculature of a subject.

After positioning aneurysm bridge 1 across the opening of aneurysm A, the device is then deployed and either temporarily or permanently implanted in the vessel. As illustrated beginning with FIG. 3B, in order to deploy aneurysm bridge 1, sheath 2 is withdrawn proximally to permit the device 1 to expand to its unconstrained configuration into contact with the inner walls of the parent vessel V. When sheath 2 is completely withdrawn from the length of bridge device 1, device 1 expands to a deployed diameter, as illustrated in FIG. 3C. Also, when sheath 2 is withdrawn from along the length of device 1, bumps 9 are no longer retained in apertures 8. Pusher 5 may then be withdrawn from the vessel V. Alternatively, pusher 5 may be left positioned in vessel V, and central lumen 7 may be utilized as a conduit or passage in a subsequent step. Further, if the user wishes to reposition device 1, sheath 2 can be advanced distally in order to resheath device 1. The steps of positioning and deploying device 1 described above can then be repeated.

Figure 2A:
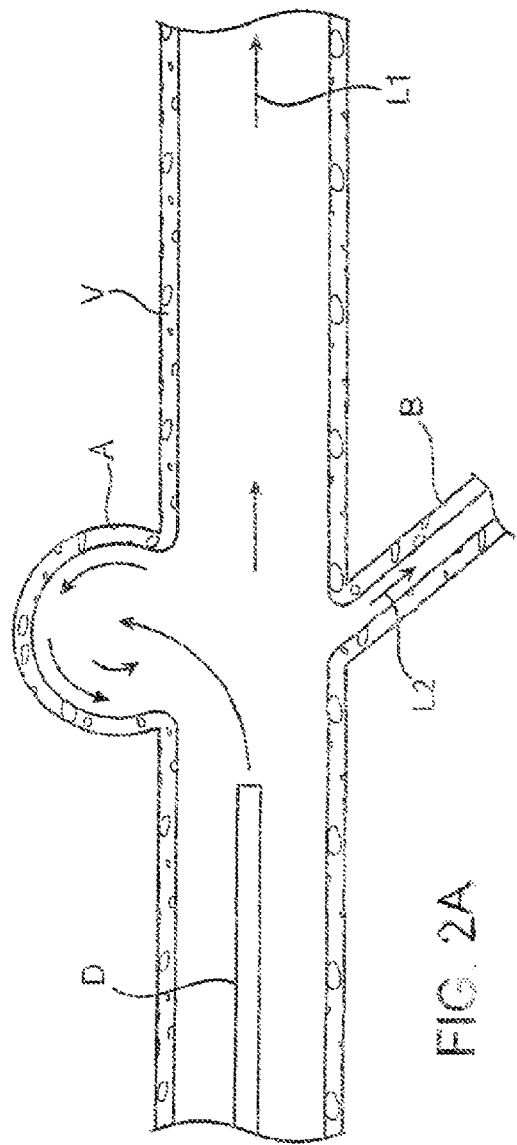
Figure 2B:
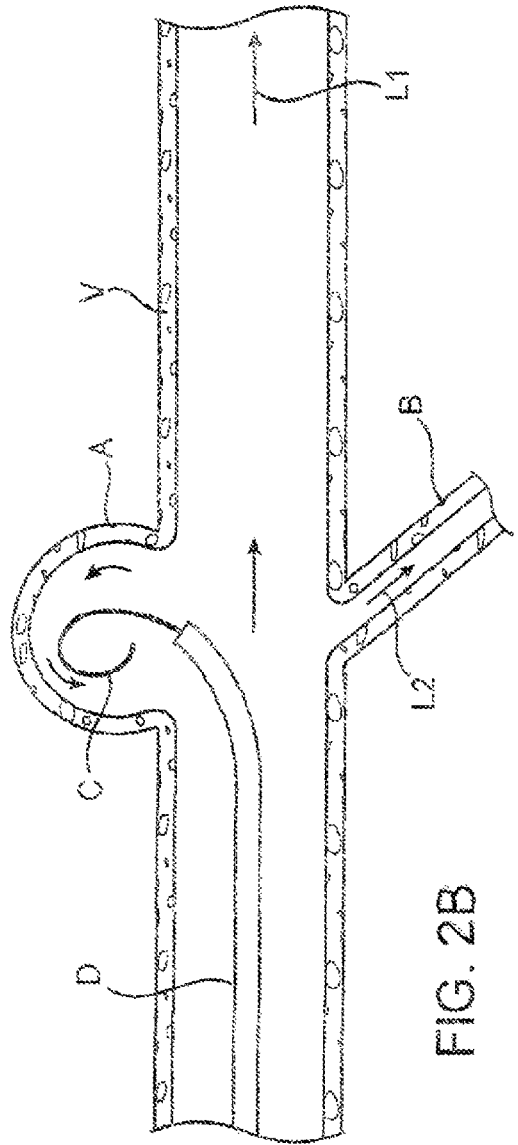
Figure 3E:
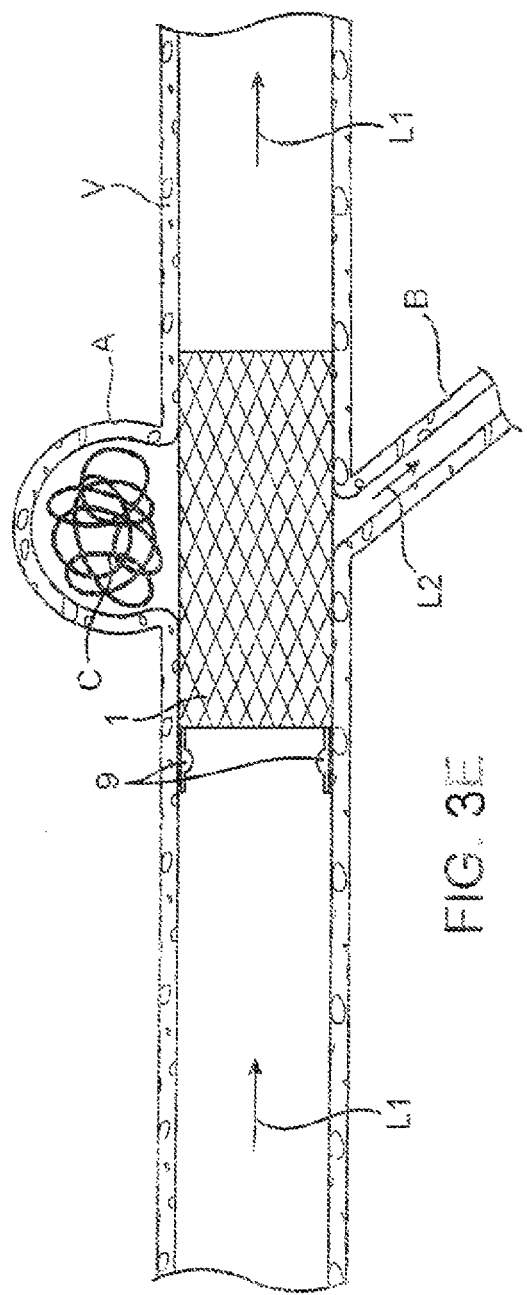

Voids in the walls of the tubular device 1 permit the catheter-based delivery of embolic coils through the walls and into the aneurysm. (Alternatively, embolic coils may be implanted according to a method in which the coils are not delivered through the voids in the wall of device 1, as described in greater detail below.) As illustrated in FIG. 3D, delivery catheter D may be positioned within vessel V (and/or alternatively within pusher lumen 7). Embolics including one or more embolic coils may then be delivered to the aneurysm, in much the same manner as described above in relation to FIGS. 2A-2C, except that they are delivered through the voids in the "walls" of the bridge 1. The position of the device 1 across the neck of the aneurysm prevents the unintended escape of embolic materials out of the aneurysm and into the parent vessel following the conclusion of the procedure (See FIG. 3E). The device remains in place in the parent vessel across the aneurysm neck during the delivery of coils, thereafter, and if desired, permanently.

Figure 4G:
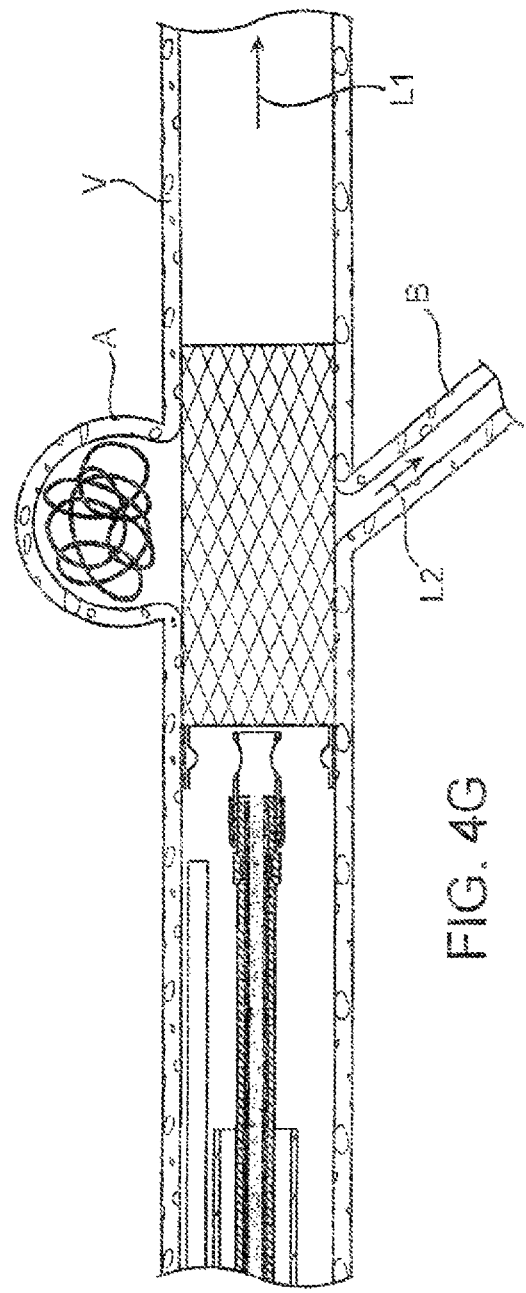

Turning now to an alternative method according to the invention, FIGS. 4A-4G illustrate exemplary steps according to the alternative method. In the steps illustrated in FIGS. 4A-4G, the aneurysm bridge 1 described above in relation to FIGS. 3A-3E is again utilized, but according to a somewhat different method than that described in the foregoing paragraphs. FIG. 4A illustrates an early step according to the invention following the introduction of delivery catheter D into a vessel V having aneurysm A. One or more embolic coils, in the elongate configuration, is constrained by and carried within delivery catheter D. The distal end of delivery catheter D is positioned proximate aneurysm A.

Following positioning of delivery catheter D proximate aneurysm A, the aneurysm bridge device 1 and accompanying delivery system are introduced into the vessel V and positioned proximate aneurysm A, generally as illustrated in FIG. 4B. In addition to aneurysm bridge device 1, the delivery system includes sheath 2 that was illustrated and discussed above. Sheath 2 retains aneurysm bridge device 1 in a reduced profiled configuration. Device 1 is capable of expanding into contact with the vessel walls, or released or deployed to a larger diameter configuration, when sheath 2 is withdrawn.

There are many similarities between the delivery system illustrated in FIG. 3B and FIG. 4B. However, the system illustrated in FIG. 4B includes alternative pusher 14. Pusher 14 may be formed of suitable polymers, metals, and/or composite materials. Pusher 14 may include any of the materials and dimensions of pusher 5 described above, but pusher 14 does not include a central lumen. A guide wire (not pictured) may also be utilized in the step of positioning the system in a vessel.

Prior to introduction into vessel V, the proximal end 3 of aneurysm bridge device 1 is disposed upon the distal end of pusher 14. Exemplary distal tips of pusher 14 are described in greater detail below in a description of FIGS. 11-14. Distal tip 4 again includes apertures 8. When loaded onto distal tip 4, device 1 is threaded over pusher 14, and positioned so that bumps 9 of its proximal end 3 are aligned with, or inserted into, apertures 8. Bumps 9 may alternatively be projections, tabs, posts, clips, or any structures, preferably male, that are suitable for engaging apertures 8. Similarly, apertures 8 may alternatively be pockets, holes, hollows, grooves, or any structures, preferably female, for receiving bumps 9. Sheath 2 retains bumps 9 in engagement with apertures 8 as it retains aneurysm bridge device 1 in a reduced profile configuration. Device 1 remains in the reduced profile configuration during tracking of the device under fluoroscopic visualization to a treatment site within the vasculature of a subject.

After positioning aneurysm bridge 1 across the opening of aneurysm A, and proximate the distal end of delivery catheter D, the device is then deployed. As illustrated beginning with FIG. 4C, in order to deploy aneurysm bridge 1, sheath 2 is withdrawn proximally to permit the device 1 to expand to its unconstrained configuration into contact with the inner walls of the parent vessel V. When sheath 2 is completely withdrawn from the length of bridge device 1, device 1 expands to a deployed diameter, as illustrated in FIG. 4D. If the user wishes to reposition device 1, sheath 2 can be advanced distally in order to resheath device 1. The steps of positioning and deploying device 1 described above can then be repeated. Pusher 5 may then be either withdrawn from the vessel V or may be left positioned in vessel V. As illustrated in FIGS. 4C and 4D, delivery catheter D remains in place proximate the aneurysm during the steps of the method described herein.

As illustrated in FIG. 4E-4F, one or more embolic coils (or other embolic material) may then be delivered to the aneurysm, in much the same manner as described above, except that they are delivered directly into the aneurysm, instead of through the voids in the "walls" of the bridge 1. The position of the device 1 across the neck of the aneurysm prevents the unintended escape of embolic materials out of the aneurysm and into the parent vessel following the conclusion of the procedure (See FIG. 4G). The device remains in place in the parent vessel across the aneurysm neck during the delivery of coils, thereafter, and if desired, permanently.

Figure 5:
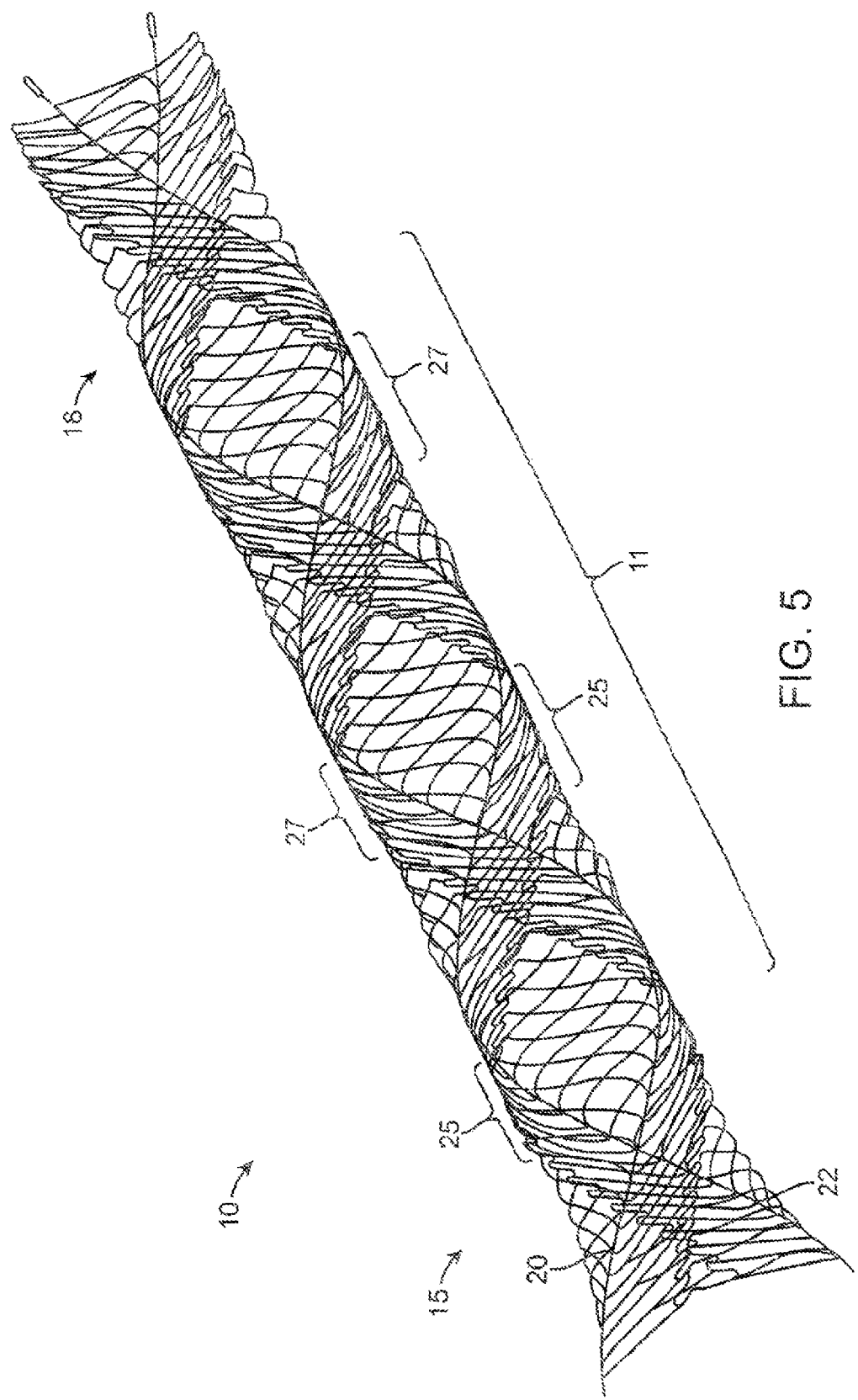
FIG. 5 is a perspective view of a finished device according to the invention, in a deployed configuration that results when the device is not placed in a vessel prior to deployment, hereinafter referred to as a "deployed in air".

Details of an aneurysm bridge device according to the invention are illustrated in FIG. 5. Aneurysm bridge 10 is illustrated in a deployed "in air" configuration. Aneurysm bridge 10 is a more or less tubular device capable of being retained in a constrained form or shape prior to deployment, and then expanded (or permitted to expand) into contact with the walls of a vessel when deployed. Consequently, it may be positioned and delivered using a variety of methods similar to those summarized above in conjunction with the description of FIGS. 3A-4G. As described in detail below, aneurysm bridge 10 has many advantages over prior art devices for improved delivery, deployment, retraction, repositioning, and redeployment.

Aneurysm bridge 10 may be constructed from any number of compositions having suitable biocompatibility and strength characteristics. In the embodiment illustrated in FIG. 5, aneurysm bridge 10 is constructed from Nitinol® with "shape memory" or superelastic characteristics to optimize self expansion of the device upon deployment. Aneurysm bridge 10 is constructed by cutting features into a Nitinol tube. For example, a tube of 3.5 mm outer diameter and 0.005 inch thickness may be cut in a predetermined pattern of bands, struts, and/or connectors. Examples of suitable patterns are illustrated below in FIGS. 9 and 10, though variations on the patterns are within the scope of the invention. After the features are cut into the tube, the tube is twisted and shape set. It has been found that a helical arrangement resulting from the twist helps the deployed device conform to the vessel walls, and it also improves the ability of the device to resist kinking.

An aneurysm bridge according to the invention may be dimensioned in any number of suitable sizes and lengths, depending upon the location of the aneurysm, variances in patient anatomy, and the size and shape of the aneurysm. Aneurysm bridge 10 of FIG. 5 in its expanded configuration is approximately 2.0-6.0 mm at its maximum outer diameter, and between 10-45 mm in length. Aneurysm bridge 10 can be described while viewing FIG. 5 from left to right, with its proximal end 15 on the left side of the figure, its distal end 18 on the right, and a central region 11 disposed therebetween. As described in greater detail below in conjunction with a description of FIGS. 7-7C, generally tubular aneurysm bridge 10 has a generally ovular shaped cross section at its proximal end 15 and its distal end 18 when it is deployed in air. It is however generally circular in cross section throughout most of its central region 11. When bridge 10 is deployed in a vessel, it generally takes the shape and cross section of the vessel.

Figure 7:
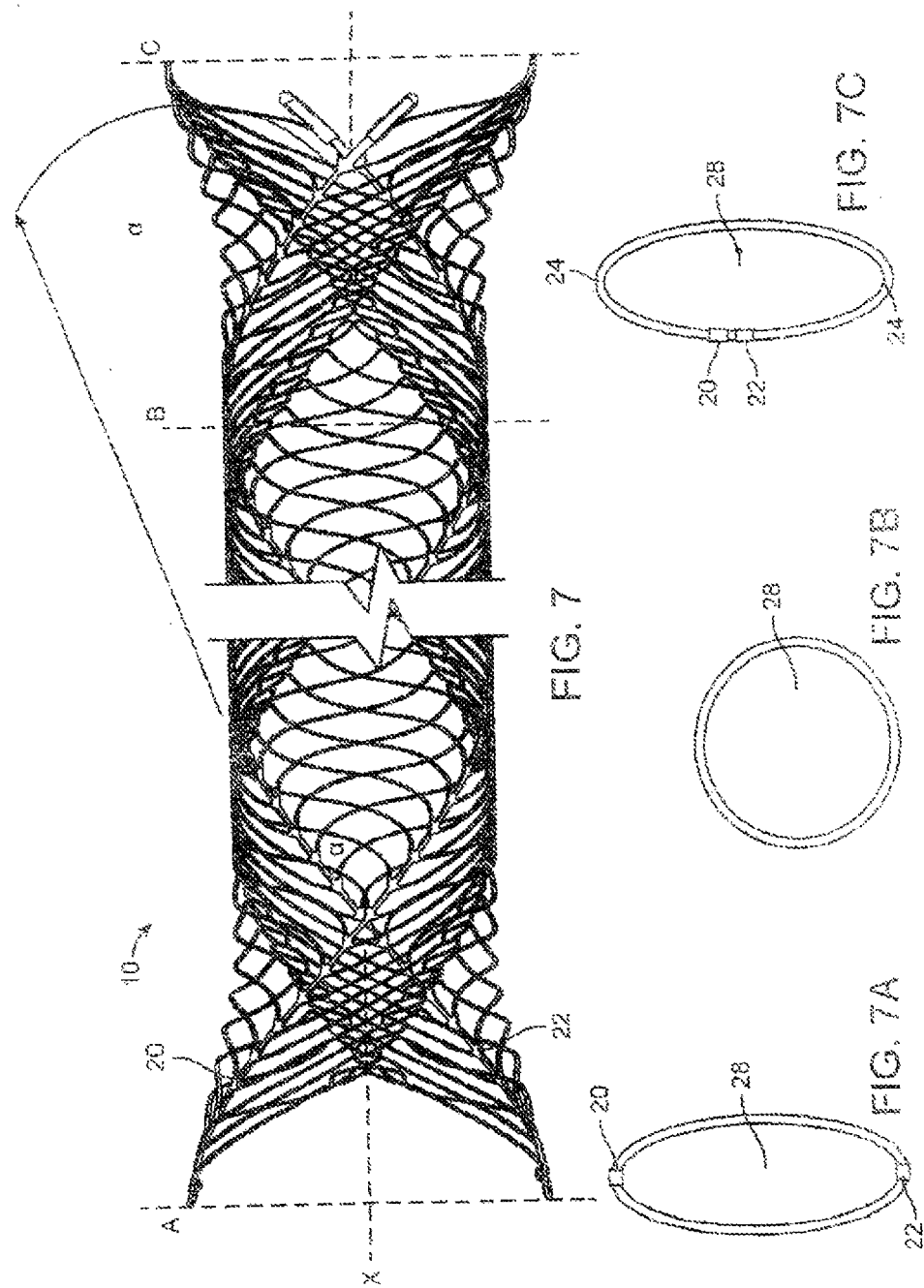
FIG. 7 illustrates a truncated side elevational view of a device according to the invention in a deployed in air configuration.

In FIG. 5, two standards 20 and 22 can be seen extending in a helical fashion from proximal end 15 to distal end 18, more or less the entire length of tubular element 10, though alternative embodiments may have a greater number of standards. The helical array of aneurysm bridge 10 may be imparted to a cut tube by grasping standards 20 and 22 and applying a circumferential twist. (The extent of circumferential twist can be characterized in terms of the resulting angle of standards 20 and 22 to the longitudinal axis of device 10, and is illustrated in FIG. 7 below). Standards 20 and 22 have a width in the range of 0.0020-0.0050 inch, preferably between 0.0030-0.0045 inch, and impart axial and columnar strength upon aneurysm bridge 10. The standards may also be used to provide axial force to the device if it is necessary to reposition the device after partial deployment within the vessel as discussed above. Standards 20 and 22 may further be equipped with features to facilitate loading of the finished device 10 into a sheath.

Standard 22 defines a portion of first helical spine 25. First helical spine 25 extends in a helical fashion along the length of aneurysm bridge 10 from proximal end 15 to distal end 18 as a result of the circumferential twist applied to standards 20 and 22. Similarly, standard 22 defines a portion of second helical spine 27. Second helical spine 27 extends in a helical fashion from proximal end 15 to distal end 18 of aneurysm bridge 10. First helical spine 25 and second helical spine 27 impart columnar strength and uniform, reduced size gap spacing along the length of the device 10. The specific features that define first helical spine 25 and second helical spine 27 will be described in detail in relation to FIGS. 8 and 9, in which the features are more easily viewed.

Figure 6:
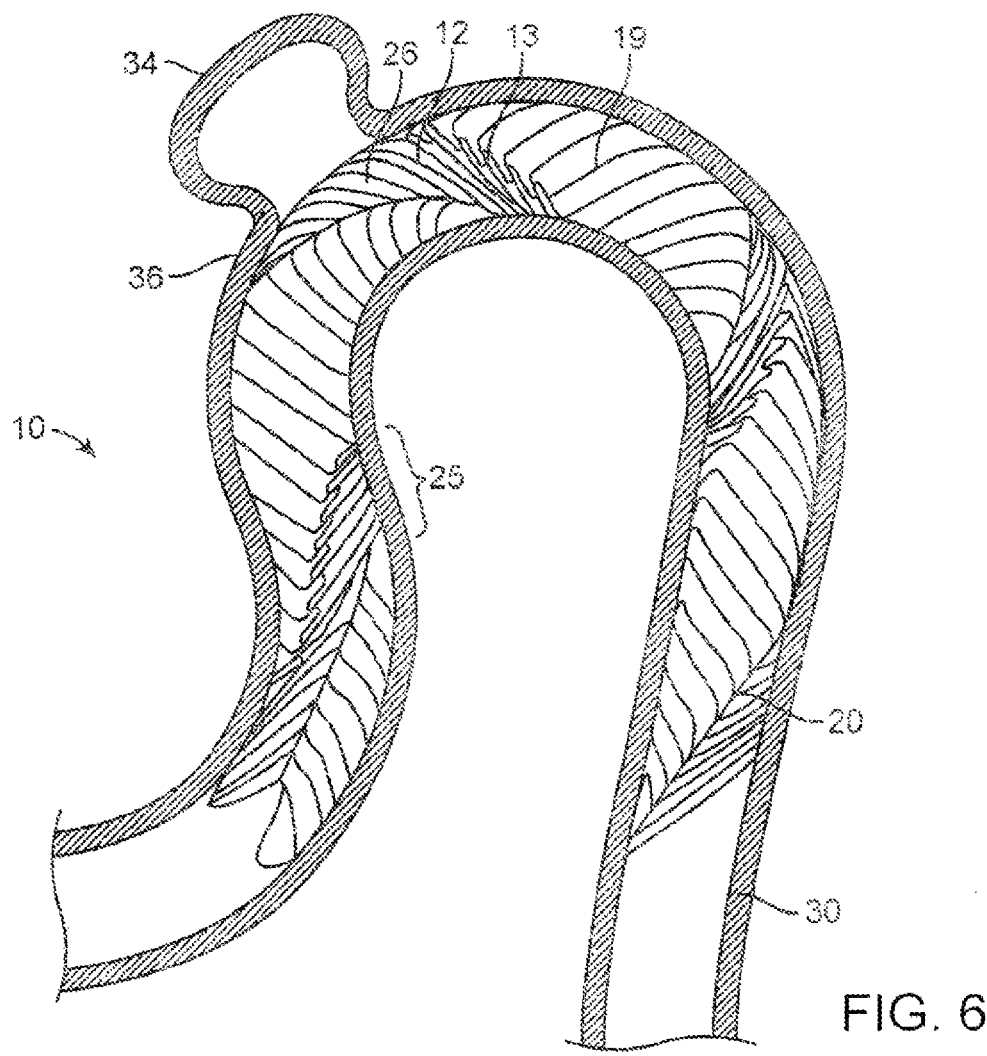
FIG. 6 illustrates a side view of a device according to the invention deployed within a curved, transparent model vessel.

Among the advantages of the invention herein are its superior, kink-resistant, reversible trackability and reversible deployability within tortuous vasculature. In order to illustrate the superior tracking and reliable deployment of the system, device 10 is shown deployed within a transparent vessel model 30 in FIG. 6. Transparent model vessel 30 has a curved configuration and model aneurysm 34 located on the "outer" side of curve 36. Device 10 was tracked through curve 36 and across the neck of aneurysm 34. Aneurysm bridge 10 was permitted to expand radially outwardly to closely meet the walls of the vessel model. And despite the curved configuration of the vessel model, aneurysm bridge device readily deploys to contact the walls of the lumen. Moreover, when deployed in a curved vessel, the features of device 10, (which are described more specifically below in conjunction with a discussion of FIG. 9) are disposed in a uniform, orderly configuration. No portion of aneurysm bridge device 10 bulges or protrudes into aneurysm 34. Consequently, aneurysm bridge device 10 can be repositioned and redeployed readily if needed, or withdrawn completely from the vessel. And aneurysm bridge device 10 provides orderly gaps between struts or bands through which occlusion coils (not pictured) may be both delivered to aneurysm 34 and prevented from escape therefrom.

FIG. 7 illustrates other aspects of aneurysm bridge 10 from a truncated side elevational view. Firstly, the twist angle mentioned above in relation to FIG. 5 is more easily viewed in FIG. 7. Twist angle α is illustrated as the angle between standard 20 and longitudinal axis x of device 10. Twist angle α is between 15° and 40°, and preferably between 20° and 35°, in either a clockwise or a counterclockwise direction. A particular twist angle may be imparted on device 10 after pattern features illustrated in FIGS. 9 and 10 below are cut into a Nitinol tube.

FIGS. 7A-7C illustrate cross sectional shapes of device 10 (when it is deployed in air), along lines A, B and C of FIG. 7 above. FIG. 7A illustrates the cross section of proximal end 15 at Detail A. At proximal end 15 of aneurysm bridge 10, standard 20 is generally opposite standard 22. FIG. 7B illustrates the cross section of central region 11 at Detail B. And FIG. 7C illustrates the cross section of aneurysm bridge 10 at detail C. At distal end 18, standards 20 and 22 intersect one another along a wall of aneurysm bridge 10. Apexes 24 are disposed opposite one another, at the narrowest portions of the oval. Central lumen 28, which extends the length of tubular element 10, is consequently ovular in cross section at the proximal and distal ends of aneurysm bridge 10, and circular in cross section in the central region of the device.

Figure 8:
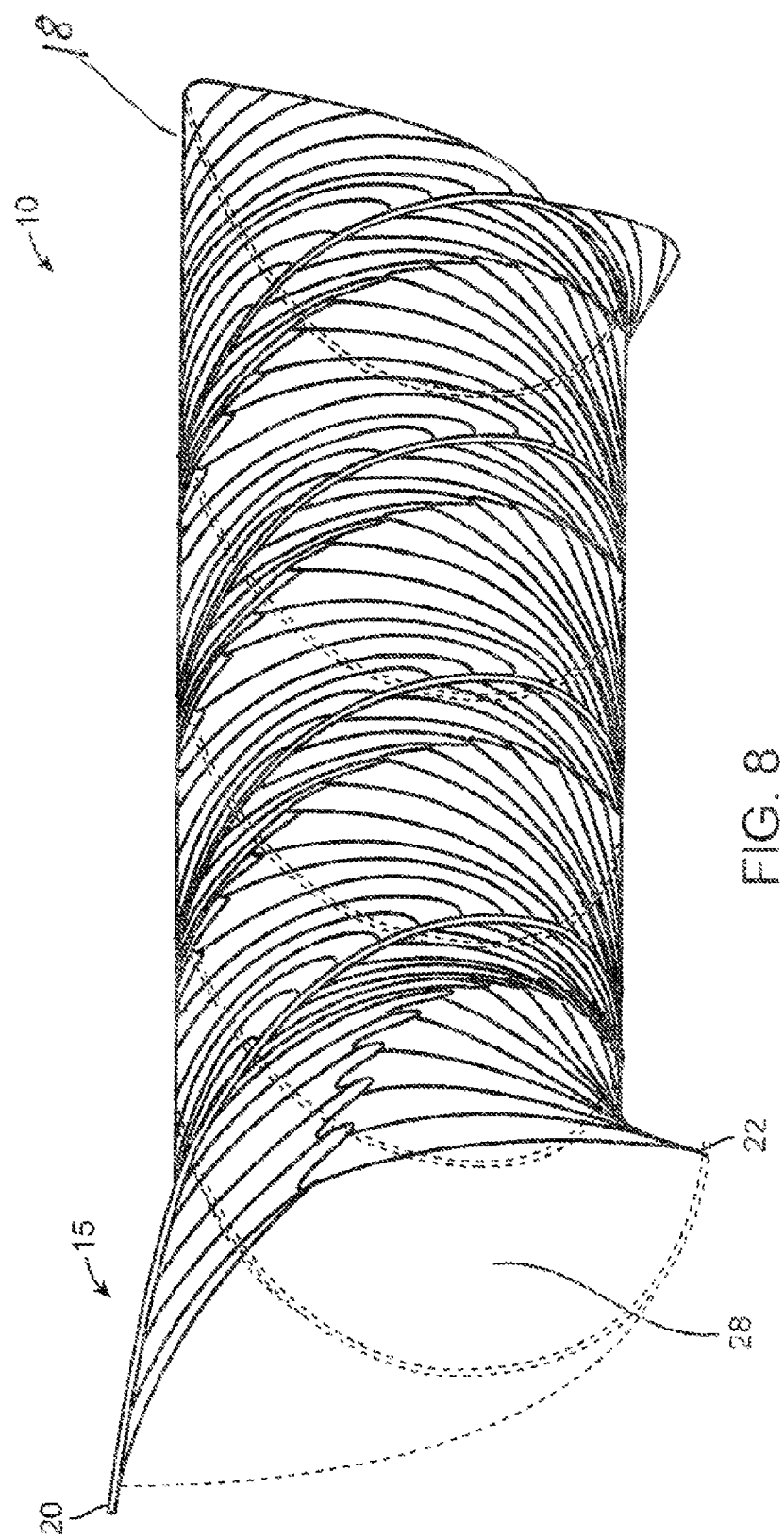
FIG. 8 is a perspective proximal end view of a finished device according to the invention in a deployed in air configuration.

FIG. 8 illustrates aneurysm bridge 10 from a perspective view of proximal end 15, revealing central lumen 28. (For clarity, the portion of bridge 10 on the "back side" of lumen 28 is illustrated merely by dotted helical lines.) Distal end 18 is essentially facing away from the viewer in FIG. 8. Bridge 10 is again shown deployed in air, and proximal end 15 has a generally ovular cross section. At proximal end 15, the proximal-most ends of standards 20 and 22 lie essentially opposite one another, along the narrowest portions of the oval.

Figure 9:
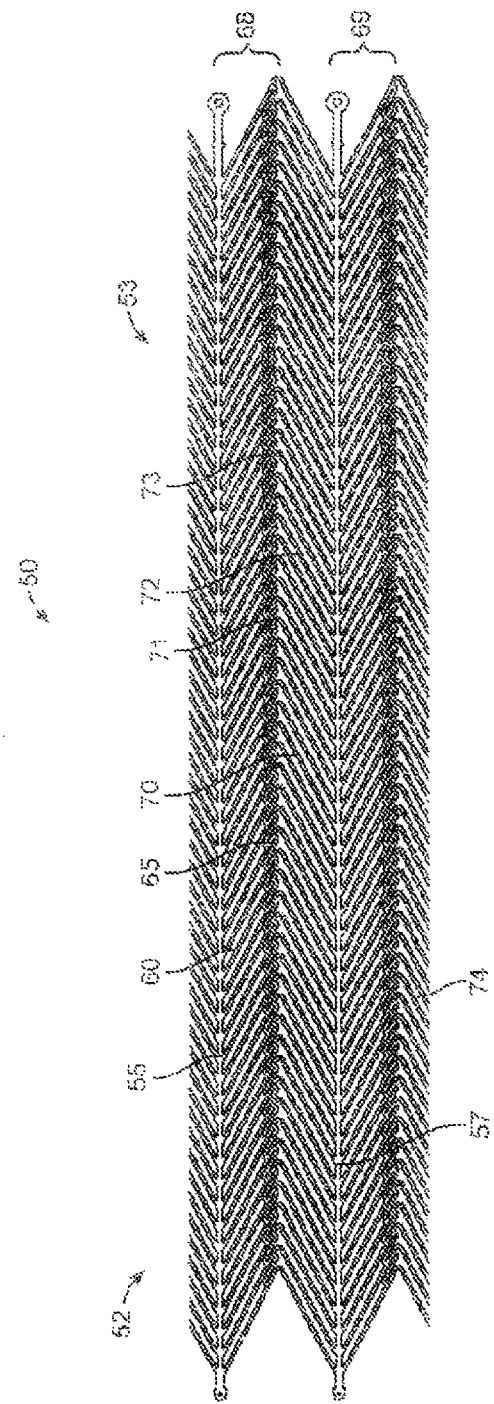
FIG. 9 is a plan view of a cut pattern for manufacture of a device according to the invention. Although devices according to the invention are preferably cut from tubular structures, twisted and shape set.

FIG. 9 illustrates an example of a cut pattern used to make a device according to the invention. Although an aneurysm bridge according to the invention is a generally tubular device shape set into a twisted configuration, FIG. 9 illustrates the device as though, before being shape set into a twist, it has been cut along its length and laid flat so that its features may be more easily viewed. Cut pattern 50 has a proximal end 52 and a distal end 53. Cut pattern 50 also has standards 55 and 57. Standard 55 and standard 57 have a similar set of features arrayed in a repeating pattern. For ease of reference, these features will be described especially in relation to standard 55, though standard 57 is also oriented to bands, struts or connectors having generally the same features. Extending laterally or diagonally from standard 55 is a plurality of bands 60. Bands 60 have strut widths in the range of 0.00050-0.00150 inch, and preferably between 0.00060-0.00120 inch. Bands 60 in turn extend to define S-connectors 65. Standard 55, bands 60 and S-connectors 65 define a first spine 68. Second spine 69 is defined by the corresponding features in conjunction with standard 57. In the cut pattern 50, spines 68 and 69 are generally straight. In a finished device, however, a circumferential twist will be shape set into the device, placing spines 68 and 69 in a helical configuration.

Connected to the other ends of S-connectors 65 are bands referred to as V-struts 70. Each V-strut 70 includes a short leg 71, a long leg 72, and an apex 73 therebetween. Apexes 73 are disposed pointing toward distal end 53. Though other geometries are possible within the scope of the invention, the resulting lattice of first spine 68, V-struts 70, second spine 69 and V-struts 74 will define the skeletal "walls" of the generally tubular aneurysm bridge and the shape and size of voids within the walls.

The function of S-connectors 65 can be described as limiting the expansion between bands 60. The expansion limiting function can most easily be viewed in FIG. 6. Aneurysm bridge 10, deployed in curved model vessel 30, has bands 12 and S-connectors 13. The tighter spacing between bands 12 is illustrated in comparison to the wider spacing of V-struts 19. S-connectors 13 tighten the gaps in the walls of the device, effectively reducing the size of gaps 26 by roughly half, thereby providing a barrier to coils that may be implanted into aneurysm 34. S-connectors 13 also prevent bands 12 and V-struts 19 from "poking" or protruding into aneurysm 34, an important advantage if the device must be repositioned, especially when the aneurysm is disposed in a curved vessel, as in the example of FIG. 6. The closely spaced and generally uniform array imparted by S-connectors 13 is imparted along the length of first helical spine 25 (and second helical spine 27, which is not visible in FIG. 5), and consequently along the length of aneurysm bridge 10.

The function of V-struts 19 can be characterized as maximizing the flexibility of the device 10. The flexibility imparted by V-struts 19 is very important for accommodating the flexure of the device both prior to deployment and over the life of the device. Prior to deployment of the device, most of the stress imparted on the device occurs during crimping down and loading the device into a sheath, and then tracking the crimped device through tortuous vasculature while crimped down and sheathed. Following deployment of the device within the vessel, most of the stress imparted on the device is a result of the ongoing, long term expansion and contraction due to pulsation of the vessel. In both configurations, the majority of the stress on the device is absorbed by the V-struts 19. It is desirable for the device to be able to flex at the "V"; otherwise the stress may break the device, or deform the device beyond its ability to recover, or otherwise cause the device to fail.

Figure 10:
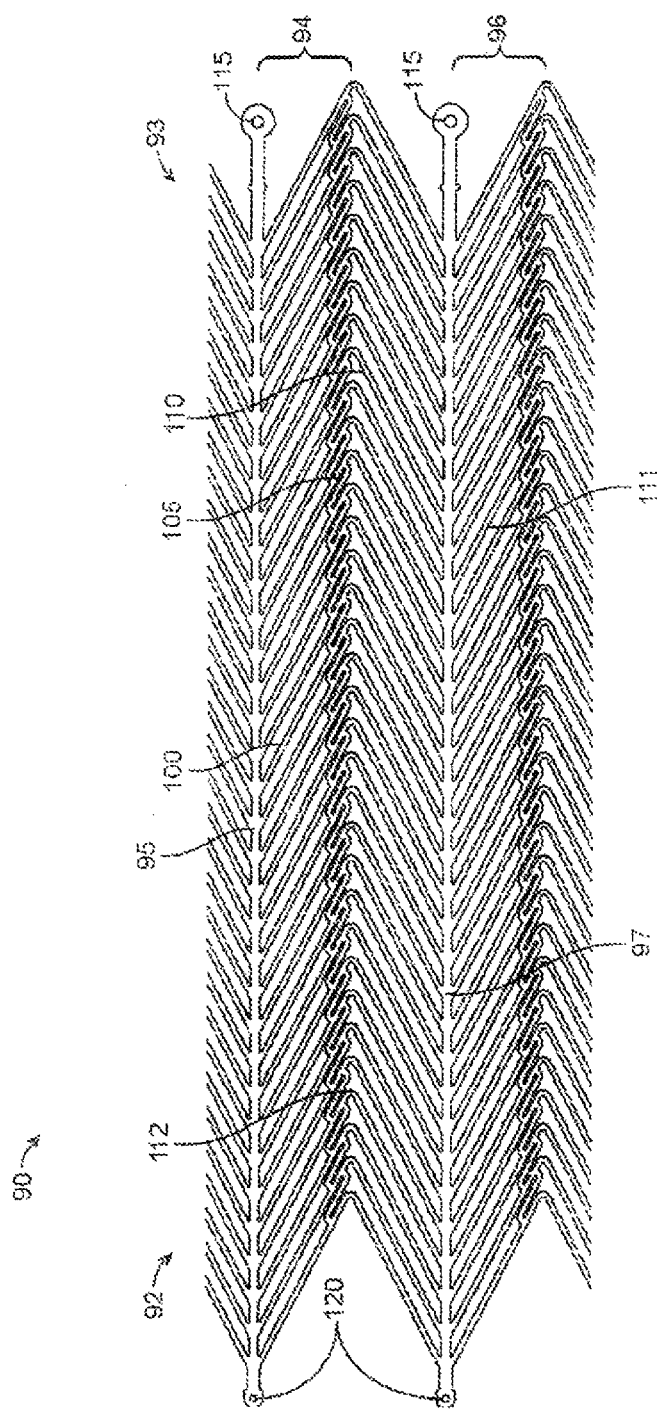
FIG. 10 is a plan view of a cut pattern of an alternative embodiment according to the invention. Although the bridge devices are preferably tubular structures, cut from a tube, twisted and shape set.

The specific structures of bands 12, S-connectors 13 and V-struts 19 of FIGS. 5-8 are similar to the corresponding features of FIGS. 9 and 10, but can be most easily viewed in FIG. 10. FIG. 10 illustrates an alternative embodiment according to the invention. Similar to FIG. 9, it illustrates a cut pattern of a generally tubular device as though it were cut along the length of the tube before the tube has been shape set, and laid flat so that the features of the pattern may be more easily viewed. Cut pattern 90 has proximal end 92, distal end 93, and standards 95 and 97. Cut pattern 90 has a lesser number of bands 100 than does cut pattern 50 described above. Cut pattern 90 has a correspondingly fewer number of S-connectors 105 and V-struts 110. Cut pattern 90 accordingly will form a shorter length device than cut pattern 50.

An important similarity between the embodiment of FIG. 10 and other embodiments is that S-connectors 105 perform the same gap-limiting function without sacrificing needed flexibility. In order to perform this function, S-connectors 105 are disposed between bands 100 and V-struts 110, and specifically very near apexes 112 of V-struts 110. V-struts 110 consequently have a short leg 114 and a long leg 116. S-connectors 110 thereby maintain close spacing between bands 100, while permitting flexure of apexes 112. Because most of the stress during flexure of the device made from cut pattern 90 is absorbed by apexes 112, it is important that the S-connector not completely prevent flexure of apexes 112. The positioning of 5-connectors illustrated in FIG. 9 help define first spine 94 and second spine 96, yet permit flexure of V-struts 110. Apexes 112 additionally point in the direction of distal end 93, facilitating resheathing of the device if needed.

Figure 11A:
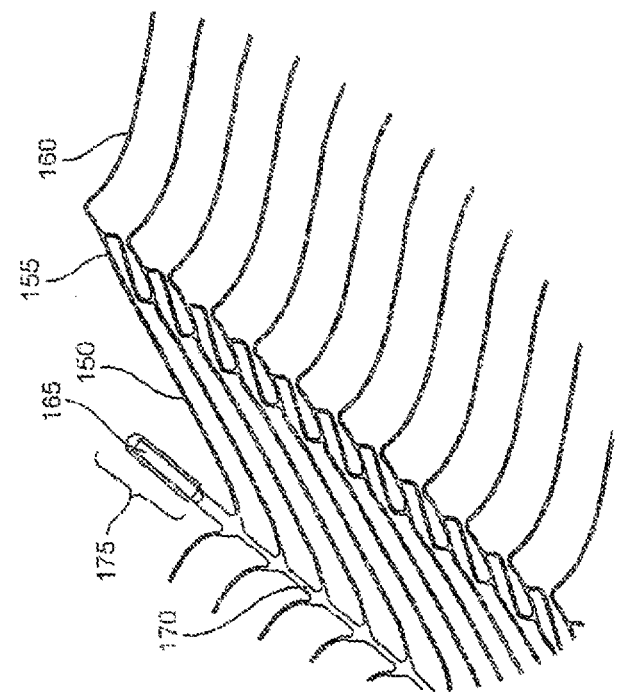
FIGS. 11A-11B are enlarged views of Details A and B of FIG. 10.
Figure 11:
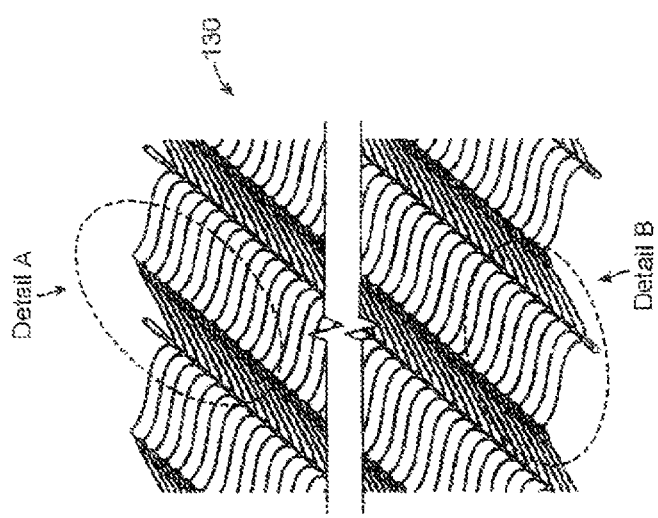
FIG. 11 is a truncated plan view of an embodiment according to the invention. Although the bridge devices are preferably tubular structures.

FIG. 11 illustrates a truncated view of a cut pattern to which a right hand twist has been applied. Cut pattern 130 is illustrated as though a twisted tubular aneurysm bridge according to the invention were cut along its axis and unrolled to better display its features. More easily viewed in FIG. 11A, Detail A, taken from a distal portion of cut pattern 130 of FIG. 11, reveals the structure of bands 150, S-connectors 155, and V-struts 160. Also visible in FIG. 11A is marker 165, which is disposed on the distal end of standard 170. The distal extension 175 of standard 170 is between 0.0200-0.110 inch, and preferably between 0.0300 and 0.1050 inch in length.

Figure 11B:
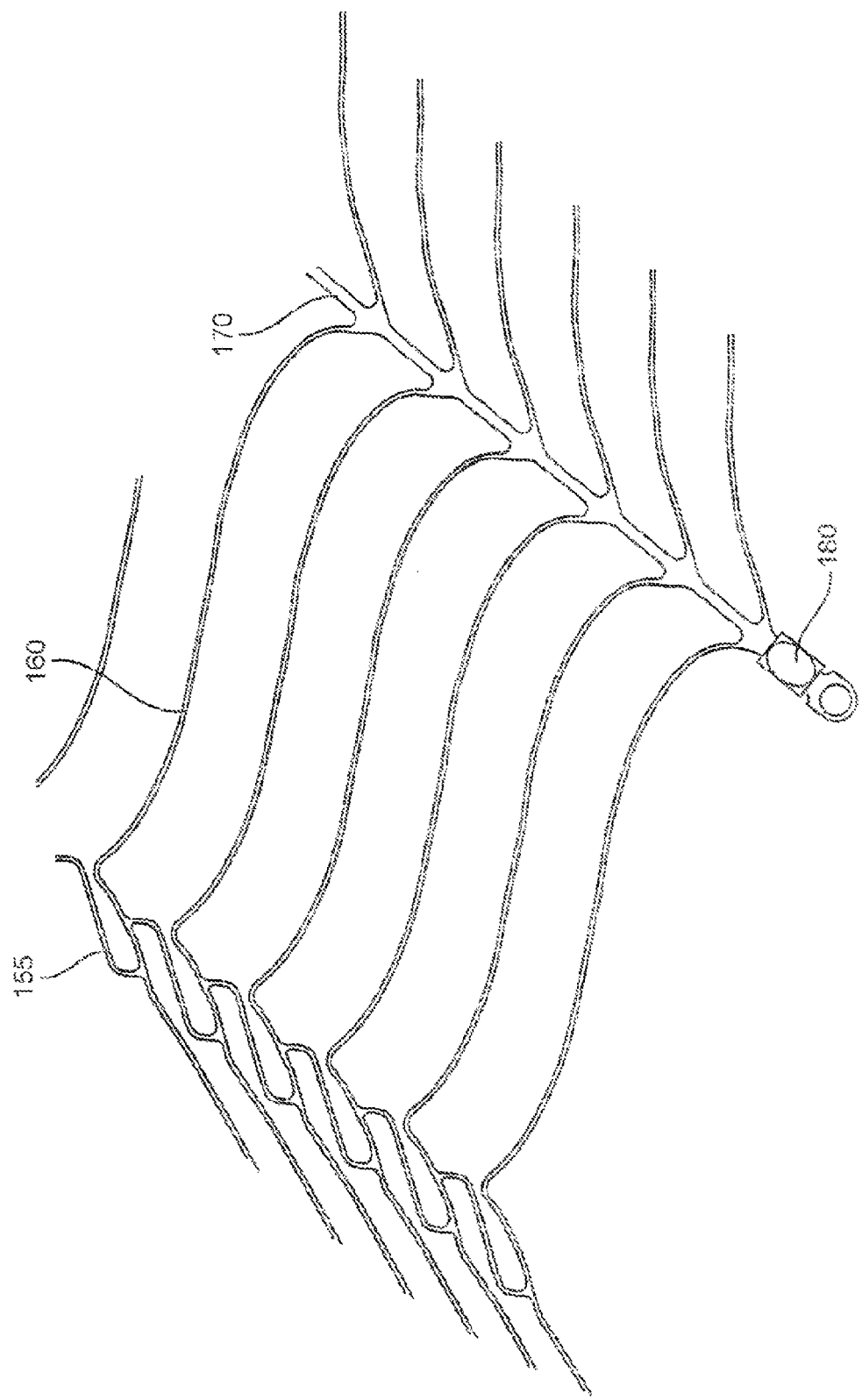

FIG. 11B is an enlarged view of Detail B, taken from a proximal region of FIG. 11, to better illustrate some of its features. Again S-connectors 155 are visible, as are V-struts 160, and standard 170. Affixed near the proximal end of standard 170 is bump 180 (shown from a top view of bump 180). As mentioned above, bump 180 is useful in loading a finished device on the distal end of a pusher prior to retaining the device with a sheath (see FIGS. 3A-3C).

Figure 12:
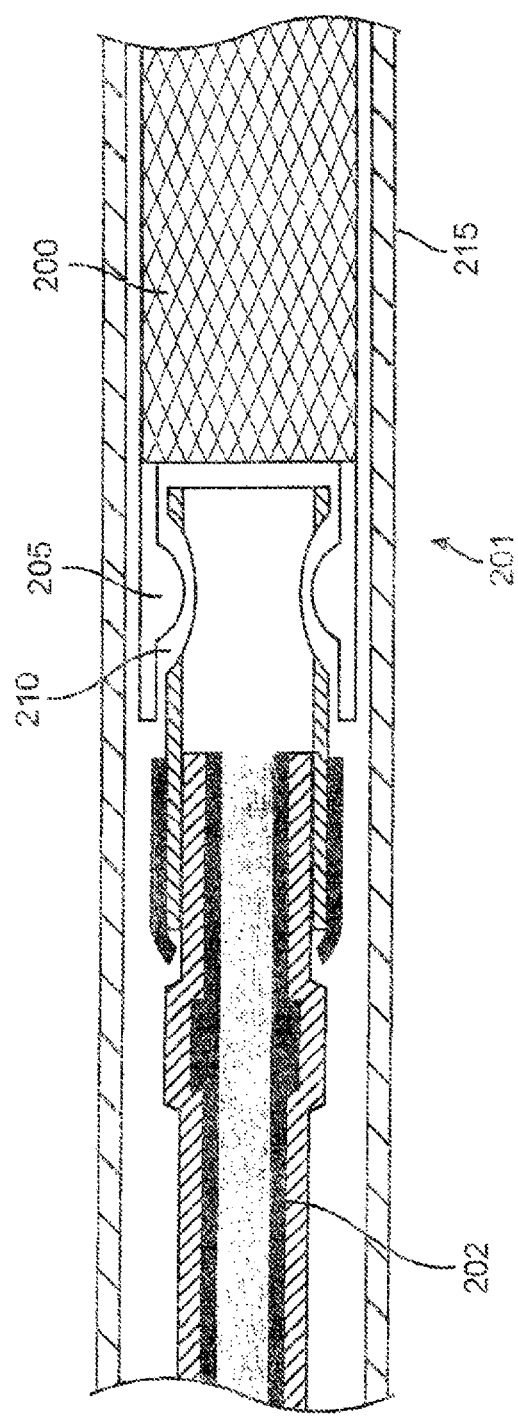
FIG. 12 is a side elevation, partial cross sectional view of the distal end of a pusher catheter according to the invention, shown within a vessel and with the proximal end an aneurysm bridge device according to the invention mounted thereon.

See also FIG. 12, showing an enlarged schematic illustration of a device 200 according to the invention mounted on a pusher and retained by a sheath. Proximal end 201 of aneurysm bridge 200 is shown mounted on the distal end of a pusher 202. Bumps 205 are seen in engagement with apertures 210. Sheath 215 retains aneurysm bridge 200 in its reduced profile delivery configuration, and consequently keeps bumps 205 in engagement with apertures 210 until either proximal withdrawal of sheath 215, or until pusher 202 pushes the device out of the end of sheath 215.

FIG. 13 is a perspective view of a pusher tip 300 that is not affixed to the distal end of a pusher. Pusher tip 300 has a central lumen 305, and three apertures 310. A greater or lesser number of apertures are within the scope of the invention. Similar to the apertures described in relation to FIGS. 10-11 above, apertures 310 permit the engagement of bumps on the proximal end of an aneurysm bridge device.

Legs 315 and eyelets 317 permit the attachment of pusher tip 300 onto the distal end of a pusher.

FIG. 13 is a perspective view of an alternative embodiment of a pusher tip according to the invention. Pusher tip 400 has central lumen 405 and two apertures 410 which can accommodate bumps on the proximal end of an aneurysm bridge device, to enhance retention of the device on the distal end of a pusher until deployment of the device at a desired time. Legs 415 and eyelets 417 enhance attachment of pusher tip 400 on the distal end of a pusher.

It should be recognized that a number of variations of the above-identified embodiments will be obvious to one of ordinary skill in the art in view of the foregoing description. Accordingly, the invention is not to be limited to those specific embodiments and methods of the present invention illustrated and described herein. Rather, the scope of the invention is to be defined by the claims and their equivalents.

What is claimed is:

1. An intravascular device comprising:
   a tubular element that is radially expandable from a compressed profile configuration to an expanded configuration, said tubular element comprising a wall, a proximal end, a distal end and a central portion therebetween;
   the tubular element further comprising at least two shape set twisted elongate standards extending in a helical fashion along the wall from the proximal end to the distal end when the tubular element is in the expanded configuration; and
   the tubular element further comprising:
   (i) a first plurality of V-shaped bands, each band including at least one end connected to a first elongate standard and a second end connected to another elongate standard, wherein the first elongate standard, the other elongate standard, and the first plurality of bands together define a first helical spine, wherein axially adjacent V-shaped bands are separated by a gap and at least some of the axially adjacent V-shaped bands are connected by S-shaped connecting members; and
   (ii) a second plurality of V-shaped bands, each band including at least one end connected to a second elongate standard and a second end connected to another elongate standard, wherein the second elongate standard, the other elongate standard, and the second plurality of bands together define a second helical spine, wherein axially adjacent V-shaped bands are separated by a gap and at least some of the axially adjacent V-shaped bands are connected by S-shaped connecting members.

2. The intravascular device according to claim 1 wherein at the proximal end, a first standard is disposed along a first side of the wall, and a second standard is disposed along an opposing side of the wall, and near the distal end, the first standard crisscrosses the second standard.

3. The intravascular device according to claim 1 wherein when said device is in said expanded configuration, said tubular element comprises a generally oval cross section near said proximal end and said distal end, and a generally circular cross section near said central portion.

4. The intravascular device according to claim 1 wherein at least some of said V-shape bands of the first and second pluralities of bands comprise an apex disposed between said one end and a second end of said band, whereby said band can flex at said apex.

5. The intravascular device according to claim 1 wherein said V shaped-bands comprise further comprise S shaped connecting-members, and-said S-shaped connecting members are disposed near said apexes, but not upon said apexes.

6. The intravascular device according to claim 1 wherein said tubular element is cut from a length of tubing according to a repeating pattern of bands and gaps between bands, and wherein in said pattern, the elongate standards extend parallel to one another from the proximal end to the distal end.

7. The intravascular device according to claim 1 wherein said tubular element has a longitudinal axis and at the least two elongate standards are oriented in opposite directions at angles of between 15° and 45° to said longitudinal axis when said tubular element is in said expanded configuration.

8. The intravascular device according to claim 1 wherein in addition to said first and second helical spines, said wall is defined by said bands and said at least one gap between said bands.

9. The intravascular device according to claim 1, wherein when said device is in said expanded configuration, said wall comprises a plurality of gaps between said first legs and said second legs, wherein said gaps between said first legs comprise a first size, and said gaps between said second legs comprise a second size that is larger than said first size.

* * * * *